(12) United States Patent
Fine et al.

(10) Patent No.: US 11,672,938 B1
(45) Date of Patent: Jun. 13, 2023

(54) START-UP PROTOCOLS FOR NITRIC OXIDE DELIVERY DEVICE

(71) Applicant: VERO Biotech LLC, Atlanta, GA (US)

(72) Inventors: David H. Fine, Cocoa Beach, FL (US); Edward Bromberg, Orlando, FL (US); Ryan Denton, Titusville, FL (US); Jason White, Cocoa, FL (US); Lucas G. Gamero, Oviedo, FL (US); Bryan Johnson, Orlando, FL (US); Gregory Vasquez, Cocoa, FL (US); Doug Sonosky, Cocoa, FL (US)

(73) Assignee: VERO Biotech LLC, Atlanta, GA (US)

( * ) Notice: Subject to any disclaimer, the term of this patent is extended or adjusted under 35 U.S.C. 154(b) by 372 days.

(21) Appl. No.: 16/513,312

(22) Filed: Jul. 16, 2019

Related U.S. Application Data

(60) Provisional application No. 62/699,791, filed on Jul. 18, 2018.

(51) Int. Cl.
| | | |
|---|---|---|
| *A61M 16/12* | (2006.01) | |
| *A61M 16/00* | (2006.01) | |
| *A61M 16/06* | (2006.01) | |
| *A61M 16/10* | (2006.01) | |

(52) U.S. Cl.
CPC ...... *A61M 16/122* (2014.02); *A61M 16/0057* (2013.01); *A61M 16/0666* (2013.01); *A61M 2016/1025* (2013.01); *A61M 2202/0208* (2013.01); *A61M 2202/0275* (2013.01); *A61M 2205/15* (2013.01); *A61M 2205/3368* (2013.01); *A61M 2205/6018* (2013.01)

(58) Field of Classification Search
CPC .. A61M 16/10; A61M 16/1005; A61M 16/12; A61M 16/122; A61M 16/104; A61M 2202/0275; A61M 2202/0283; A61M 2016/102; A61M 2016/1035; A61M 2205/12; A61M 2205/121
See application file for complete search history.

(56) References Cited

U.S. PATENT DOCUMENTS

| | | | |
|---|---|---|---|
| 6,758,214 | B2 | 7/2004 | Fine et al. |
| 7,025,869 | B2 | 4/2006 | Fine et al. |
| 7,560,076 | B2 | 7/2009 | Rounbehler et al. |
| 7,618,594 | B2 | 11/2009 | Rounbehler et al. |
| 7,914,743 | B2 | 3/2011 | Fine et al. |
| 7,947,227 | B2 | 5/2011 | Fine et al. |
| 8,057,742 | B2 | 11/2011 | Rounbehler et al. |
| 8,173,072 | B2 | 5/2012 | Fine et al. |
| 8,268,252 | B2 | 9/2012 | Fuller et al. |
| 8,607,785 | B2 | 12/2013 | Fine et al. |
| 8,613,958 | B2 | 12/2013 | Fine |
| 8,646,445 | B2 | 2/2014 | Fine et al. |
| 8,701,657 | B2 | 4/2014 | Fine et al. |
| 8,887,720 | B2 | 11/2014 | Fine et al. |
| 9,279,794 | B2 | 3/2016 | Tolmie et al. |
| 9,982,354 | B2 * | 5/2018 | Kim ...................... B01D 53/30 |
| 10,213,572 | B2 | 2/2019 | Gellman et al. |
| 10,780,241 | B2 | 9/2020 | Fine et al. |
| 10,960,168 | B2 | 3/2021 | Fine et al. |
| 11,000,484 | B2 | 5/2021 | Fine |

(Continued)

*Primary Examiner* — Joseph D. Boecker
*Assistant Examiner* — Thomas W Greig
(74) *Attorney, Agent, or Firm* — Meunier Carlin & Curfman LLC

(57) ABSTRACT

Start-up protocols for a device and method for administering NO is described.

13 Claims, 3 Drawing Sheets

(56) References Cited

U.S. PATENT DOCUMENTS

| | | |
|---|---|---|
| 11,154,210 B2 | 10/2021 | Watts et al. |
| 11,208,326 B1 | 12/2021 | Fine et al. |
| 11,243,197 B1 | 2/2022 | Fine et al. |
| 2009/0314289 A1* | 12/2009 | Fine ............... A61M 16/16 |
| | | 128/205.27 |
| 2010/0043789 A1* | 2/2010 | Fine ............... A61M 16/10 |
| | | 128/203.12 |
| 2011/0240019 A1 | 10/2011 | Fine et al. |
| 2012/0093948 A1 | 4/2012 | Fine et al. |
| 2012/0285449 A1 | 11/2012 | Fine et al. |
| 2014/0127081 A1* | 5/2014 | Fine ............... A61M 16/12 |
| | | 422/198 |
| 2014/0127330 A1 | 5/2014 | Fine et al. |
| 2015/0328429 A1* | 11/2015 | Acker ............... C01B 21/24 |
| | | 128/202.22 |
| 2015/0335850 A1* | 11/2015 | Santhana Naidu ............... |
| | | A61M 16/1005 |
| | | 128/204.23 |
| 2016/0106946 A1* | 4/2016 | Gellman ............... A61M 16/12 |
| | | 422/642 |
| 2016/0346498 A1 | 12/2016 | Tector et al. |
| 2017/0095634 A1* | 4/2017 | Miller ............... A61M 16/12 |
| 2017/0165293 A1 | 6/2017 | Dasse et al. |
| 2017/0165294 A1 | 6/2017 | Dasse et al. |
| 2017/0165447 A1 | 6/2017 | Dasse et al. |
| 2017/0182088 A1 | 6/2017 | Dasse et al. |
| 2018/0071467 A1 | 3/2018 | Fine et al. |
| 2018/0243527 A1* | 8/2018 | Zapol ............... C01B 21/32 |

\* cited by examiner

START-UP PROTOCOLS FOR NITRIC OXIDE DELIVERY DEVICE

CROSS REFERENCE TO RELATED APPLICATIONS

The present application claims priority to U.S. Provisional Pat. App. Ser. No. 62/699,791, entitled "Start-up Protocols for Nitric Oxide Delivery Device," filed Jul. 18, 2018, the disclosure of which is incorporated herein by express reference thereto.

TECHNICAL FIELD

The invention relates to a nitric oxide delivery device.

BACKGROUND

Nitric oxide (NO), also known as nitrosyl radical, is a free radical that is an important signalling molecule. For example, NO can cause smooth muscles in blood vessels to relax, thereby resulting in vasodilation and increased blood flow through the blood vessel. These effects can be limited to small biological regions since NO can be highly reactive with a lifetime of a few seconds and can be quickly metabolized in the body.

Some disorders or physiological conditions can be mediated by inhalation of nitric oxide. The use of low concentrations of inhaled nitric oxide can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide can also be used to treat chronic pulmonary hypertension, bronchopulmonary dysplasia, chronic pulmonary thromboembolism and idiopathic or primary pulmonary hypertension or chronic hypoxia. Since NO is known to stop the replication of bacteria, viruses and other micro-organisms, NO can also be used to treat bacterial, viral and fungal infections in mammals; for this application the NO is generally at doses greater than 100 ppm and can be given directly to the target site by means of a cannula.

Generally, nitric oxide can be inhaled or otherwise delivered to the individual's lungs. Providing a therapeutic dose of NO could treat a patient suffering from a disorder or physiological condition that can be mediated by inhalation of NO or supplement or minimize the need for traditional treatments in such disorders or physiological conditions. Typically, the NO gas can be supplied in a tank of compressed gas diluted in nitrogen gas ($N_2$). Great care should be taken to prevent the presence of even trace amounts of oxygen ($O_2$) in the tank of NO gas because the NO, in the presence of $O_2$, can be oxidized to nitrogen dioxide ($NO_2$). The NO can also be supplied from a liquid source such as $N_2O_4$, or from any other viable NO source. Unlike NO, the part per million levels of $NO_2$ gas, that can occur from the fast reaction of NO with oxygen in air, can be highly toxic if inhaled and can form nitric and nitrous acid in the lungs.

SUMMARY

In one aspect, a device for administering NO can include a NO source configured to provide NO gas to an output line, and an air source fluidly connected to the output line, wherein the air source includes a first air input line and a second air pump as a back up to the first air input line. Typically the NO gas is supplied to the patient in three general modes, first directly from the output of the NO source into a cannula that is connected to the patient; second mixed with air enhanced with oxygen feeding a cannula connected to the patient, and third connected to the output of a ventilator that is connected to the patient. The NO source could be a tank of compressed gas made up with NO diluted with pure nitrogen, where the pressure internal to the cylinder is the driving force to supply the NO gas to the cannula or ventilator line. In another embodiment, NO is formed from liquid $NO_2$, which is immediately mixed, typically with room air supplied by an internal pump and then passing the $NO_2$ in air through a convertor to reduce the $NO_2$ into NO.

In some embodiments, the first air input line can be an external air source or an oxygen enriched air source. The device can include a filter to remove particulates prior to entering the gas flow within the device.

In some embodiments, the first air input line can be a first air pump.

In some embodiments, a second air pump can be activated when the first air input line ceases to provide air to the device.

In some embodiments, the second air pump can be activated to provide additional air to the output line.

In some embodiments, the second air pump can be activated to provide for a higher output gas flow, and is mixed with the primary NO in air flow after traversing the converter to allow for proper residence time within the converter.

In some embodiments, the second air pump can be activated to provide air to flush the output line.

In some embodiments, the device can include a volume accumulator along with a restrictor configured to minimize pressure pulses.

In some embodiments, the device can include a moisture exchanger configured to remove moisture from the air. This is especially important for humid conditions when using an air pump so as to prevent moisture condensation in the instrument gas lines.

In some embodiments, the device can include a back pressure regulator.

In another embodiment, a device for administering NO can include a NO source cassette including liquid $N_2O_4$ and a conversion cartridge for converting $NO_2$ configured to provide NO gas to an output line, an air source fluidly connected to the output line, and a liquid $N_2O_4$ monitor, or "fuel" gauge, that determines the time remaining to deliver NO from the device.

In some embodiments, the liquid $N_2O_4$ monitor can monitor the current and voltage applied to the NO source cassette, the temperature of the NO source cassette, or both.

In some embodiments, the device can include a NO availability gauge that displays output from the liquid $N_2O_4$ monitor. The NO availability gauge can indicate replacement of the NO source based on the time and temperature history of the NO source cassette.

In some embodiments, a leak detector can include a monitor of voltage drawn by valves in the device to determine if there is a leak or if recalibration is necessary.

In some embodiments, the device can include a first NO sensor and a second NO sensor, each of the first NO sensor and the second NO sensor including a pump.

In some embodiments, the device can include an NO dosing display in micrograms per minute or parts per million. The NO dosing display can be corrected for formation of $NO_2$. The NO dosing display can be corrected by varying one or more of an amount of $O_2$ in a sample, a length of the sampling lines, or a volumetric flow rate in the sampling lines.

In some embodiments, the device can include a leak or blockage detector.

In some embodiments, the leak or blockage detector can monitor one or more of a change in the size and frequency of pressure pulses in the output line as measured by a pressure sensor; a special pressure line, a flow rate in the output line; or energy required to draw a sample into a sensor.

In some embodiments, the source of the NO can be from a high voltage discharge in air.

In some embodiments, the source of NO can be from a chemical reaction such as from the reaction of nitrite with an acid, or from the electrochemistry of a nitrite salt in solution, or from any chemistry that can produce NO gas.

In some embodiments, a method of administering NO can include supplying NO to a patient from a device described herein.

Other features, objects, and advantages will be apparent from the description, drawings, and claims.

DETAILED DESCRIPTION

The administration of NO according to disclosed embodiments allows for a more pure, controlled and accurate delivery of NO, which achieves enhanced efficiency, safety, and efficacy by the reduction of the $NO_2$ impurity to 0.0 ppm as measured by an electrochemical detector and to levels that are below that of ambient air as measured by Cavity Attenuated Phase Shift Spectroscopy (CAPS).

In an exemplary embodiment, the system, which is also referred to as the Acute Delivery System (ADS), uses liquid $N_2O_4$ to generate NO, which is then delivered to the patient. The delivery can be used with a nasal cannula, or by means of a ventilator or anaesthesia machine. In this embodiment, the $N_2O_4$ is heated from about 35 to 80° C. to vaporize and dissociate the $N_2O_4$ into $NO_2$ gas. The $NO_2$ gas is then passed through a narrow bore restrictor that controls the amount of $NO_2$ released to the very low required value, into an air stream that is generated from a small air pump. The air containing the $NO_2$ is then passed through a receptacle or cartridge where it is converted to NO gas for delivery to the patient. The system can be a wearable system that is configured for delivery of NO in a portable setting. The system can deliver NO with a nasal cannula or can deliver NO to a ventilator line. Examples of such receptacles or cartridges are described, for example in U.S. Pat. No. 7,914,743, entitled "Conversion of Nitrogen Dioxide ($NO_2$) to Nitric Oxide (NO)," and U.S. Pat. No. 8,057,742, entitled "Conversion of Nitrogen Dioxide ($NO_2$) to Nitric Oxide (NO)," the disclosures of which are incorporated by reference herein.

Figure 1A:
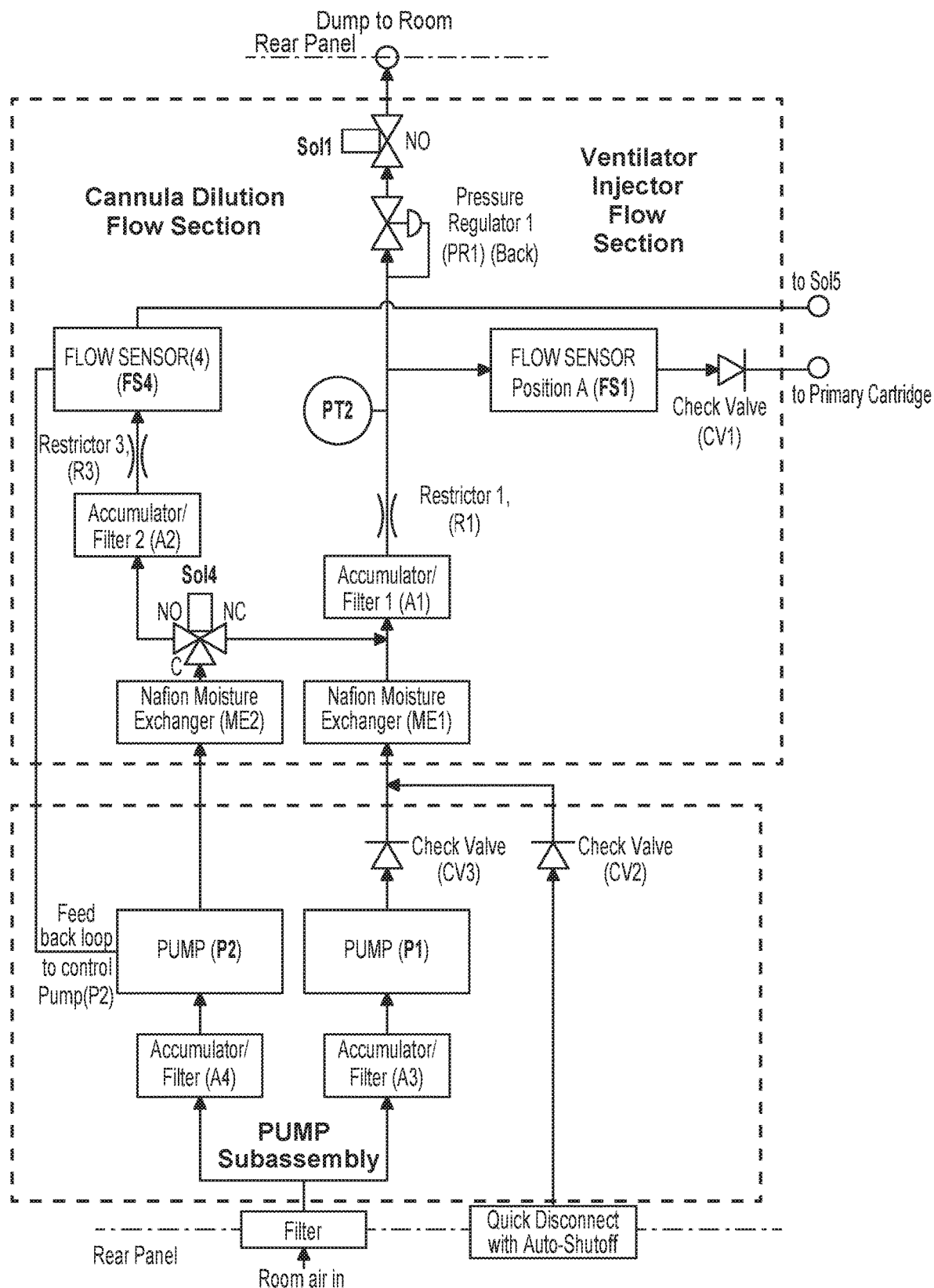
FIGS. 1A and 1B are schematic illustrations of portions of an NO delivery device, according to an embodiment.
Figure 1B:
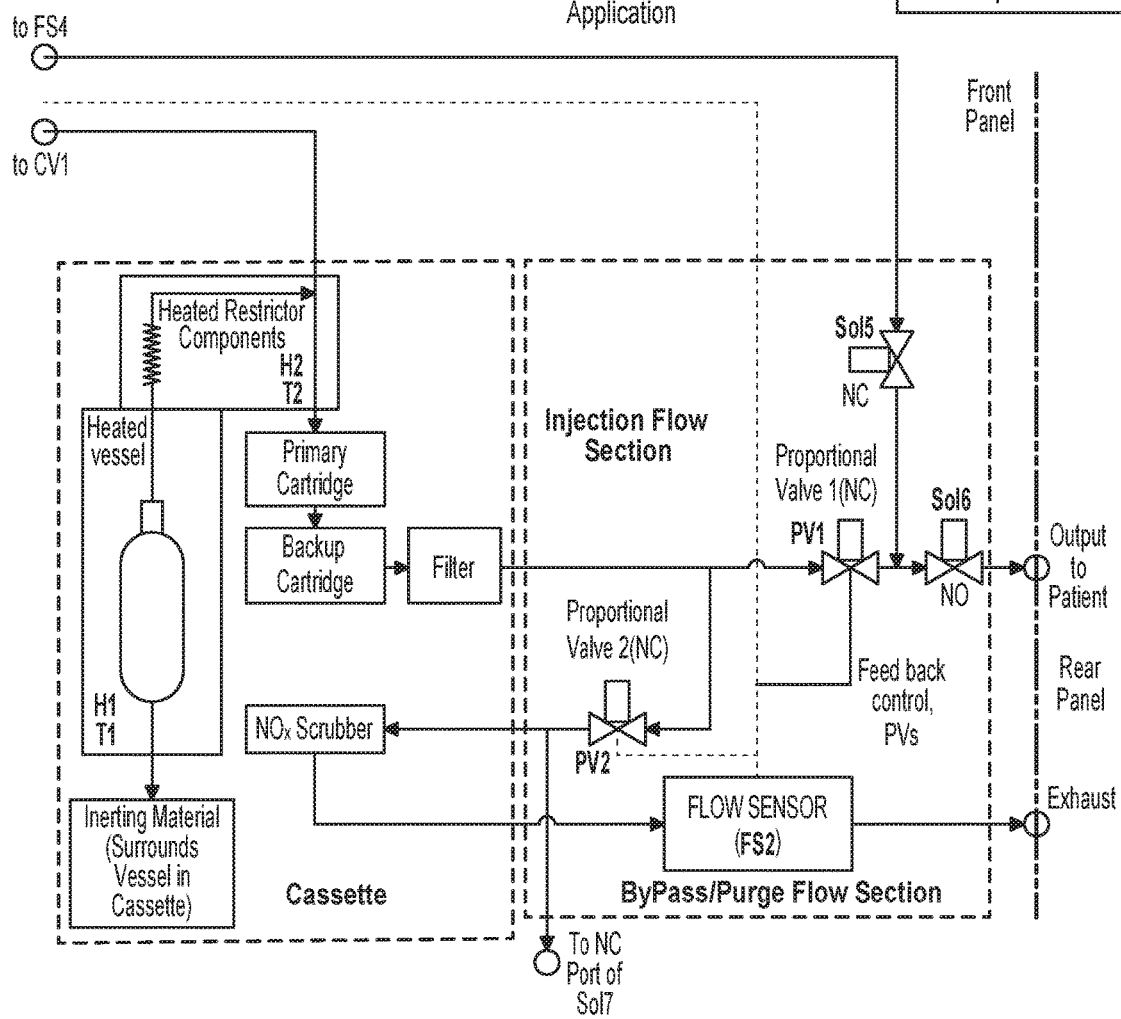

A NO delivery device according to an embodiment is shown in FIGS. 1A and 1B. In these figures the dotted lines around different subsections are purely for conceptual purposes—the illustrated components may be organized into different subsections or subassemblies. The NO delivery device can include two sources of air and/or oxygen. The source can be a combination of air pumps or hospital air or oxygen. The delivery device can only operate properly with an uninterrupted air or oxygen supply. There can be at least two independent sources of air provided in the device. Continued air supply is necessary for safety. Sudden stoppage of the delivery of inhaled NO can be life critical for many applications, including the treatment of conditions such as persistent pulmonary hypertension (PPHN). For example, without appropriate back up, failure of the air pump, P1 in FIG. 1A, could cause such a catastrophic failure and hence the need to have instantaneous back up for the safety of the patient. As shown in FIG. 1A, the backup air source can be provided with a backup pump, P2, and solenoid 4, Sol4. When the device is operating in ventilator mode, P2 is not normally used, except for a short period of time flushing the system during shutdown. Thus, if there were to be a failure of pump P1, as detected by both loss of pressure as measured by pressure transducer PT2 and loss of flow as measured by flow sensor FS1, the device software can shut off pump P1, turn on pump P2 and activate solenoid Sol4, in which case pump P2 can take over for pump P1, allowing the device to continue to provide NO therapy to the patient. The output flapper valves internal to pump P1 can act as check valves so air pumped from pump P2 does not go back through pump P1. In addition, check valves CV2 and CV3 are provided. If hospital air or oxygen is used as the primary gas source and it were to fail, then pump P1 would take instantly take over the delivery of air. If pump P1 were to fail when using pump air, or the hospital gas source were to fail, an alarm can be issued, but the console can also continue to operate with pump P1 or P2 as required, until it was time to replace a cassette, at which time a standby/backup console can be used, and the unit with the failed pump P1 could be replaced, or the problem with the hospital gas source is corrected. Check valve CV2 may be optional if the auto-shutoff feature of quick disconnect is adequate. Similarly, check valve CV3 may be optional if the flapper valves of the diaphragm pump are adequate.

Pump P2 can also be used to provide the dilution flow which may be required when a cannula is being used. This is because the cannula application can use air flows of up to 2 L/min and the cartridges within the cassette can be optimized for flows up to 1 L/min. In that case 1 L/min goes through the cassette and 1 L/min of dilution air by-passes the cassette and mixes at the output of the cassette flow, just before dosing to the patient. Flow Sensor 4 (FS4) can be used to measure the dilution flow and via a feedback loop control the voltage to pump P2 to obtain the desired flow. FS4 is identical to flow sensor FS1 and has a full scale measurement of 1 L/min. The flow through FS4 can also used after the removal of the cassette to flush the fluidic lines of any $NO_2$ to avoid any nitric acid build up that could damage the internal components.

It can be important to conduct leak detection and pump testing of the delivery system upon initiating use of the system. The leak test can be a pressure test and can be performed before or after the leak test. In a first phase of the leak test, a pressure test can be conducted. During the initial activation of the cassette, while the system is being stabilized, an internal leak check of the system can be carried out, by having both Sol5 and Sol6 closed, thus having all of the system gas flow go through both FS1 and FS2. If there were a leak the readings between these two sensors would not agree. This leak check can be carried out automatically during the start up without the user being aware. It can be part of the system check.

The system check requires solenoids Sol1, Sol5, Sol6 and proportional valve PV2 to be commanded to be in the closed position, and proportional valve PV1 in the open position and solenoid Sol4, having the common port connected to the normally open port. This leak test on startup can be checking for leaks at all of the fittings in the console, and more importantly the seals between the cassette and console since those seals will only have been made at the time that the new cassette is installed. Pump P1 can then be turned on for a fraction of a minute until the pressure as measured by pressure transducer PT2 reaches a set amount between 8 to 10 PSIG. Pump P1 can be shutoff, and the drop in pressure as measured by pressure transducer PT2 is determined. The small drop in pressure is normal and happens because the there is a small back flow through the flapper seats of the pump. If the pressure drop is less than a predetermined experimental value the system is leak tight. If the pressure decrease exceeds the set amount, it would mean that there is a leak and an error message would be generated.

In a second phase of a leak test, as soon as the cassette has been installed in the pre-heat position and the seal between the cassette and console has been made, but before activation of the ampoule, flow air can flow through flow sensor FS1 and with proportional valve PV1 closed and proportional valve PV2 open, the flow will go through the scrubbed by pass through flow sensor FS2. Or alternatively, close Sol5 and Sol6. If these two flow sensors read the identical flow, the system is leak tight, and the flow sensors are in the identical calibration. If there is a difference between the sensors and FS2 reads a higher value than FS1, then there is a flow calibration error. If FS1 reads a higher value than FS2, then either there is a calibration error, or a leak between FS1 and FS2. To distinguish between a leak and a calibration error in the second phase, the pressure test of the first phase can be reported.

In a third phase, the performance status of the pump can be assessed. During the beginning of this pressure leak detection procedure, solenoid Sol1 can be left open with the voltage to pump P1 increased slowly to determine at which voltage the pump reaches the backpressure regulator set point which is an indication of the health of pump P1 and the voltage can be a measure of determining that pump P1 while still operational is approaching its end of life. Alternatively, with solenoid Sol1 closed, the time it takes from the time pump P1 is turned on until the pressure sensor reads the backpressure set point can be determined and used as a second measure of the health of pump P1.

All of the above system checks apply equally well to any other chemistry methods that may be used for controlling the air flow for delivery of NO. These tests can be useful as part of daily self-testing or whenever a new cassette or new chemistry is inserted.

Referring to FIG. 1A, it is possible to condition the air supply to a constant humidity and to dampen air pressure pulses that are not desirable for the patient. The input air can be filtered by a polypropylene felt, for example, being 50 mm in diameter and about 1.5 mm thick. The purpose of the felt is to remove dust and dirt particles. This polypropylene filter can be replaced periodically, for example, monthly, by the user. The felt can be followed by an accumulator/filter (A3 and A4) which can be a ten micron filter in a housing with a volume of about 5 ml. This filter protects the pump from small particles not removed by the polypropylene filter, and the 5 ml volume acts as a gas volume reservoir or "capacitor" to help dampen out the pulsations from the diaphragm pump, and thus dampening the pump "noise". Since the polypropylene filter removes the dirt and dust, A3 and A4 only remove small particles and are sized to last one full year to be replaced during the normal yearly service.

Since the output of the air pump is pressurized, if the dew point of the ambient air is high, moisture condensation will occur in the lines. Moisture can react with $NO_2$ to form nitric acid, which is corrosive to the internal components. The moisture is removed by means of a Nafion moisture exchanger (ME1). Since pump P1, as well as all the other pumps in the system, are diaphragm pumps, the pump output pulsates. For gas treatment of a patient, it is desirable to have a smooth a flow as possible. To dampen out these pulsations, an RC type circuit is used with Accumulator/Filter 1 (A1) which acts as the capacitor and restrictor 1 (R1) which act as the resistor. An accumulator with filter material (identical to A3 and A4) can be used to capture any small pieces of the diaphragm or flapper seals of the pump that may be dislodged. The flow through the cassette can be measured and controlled by flow sensor 1 (FS1), a 0-1 L/min sensor, along with the proportional valves, PV1 and PV2. In order to maintain a minimum and constant pressure through the system, a back pressure regulator (PR1) can be used and can be set to a nominal 8 PSIG. A minimum flow is set through pump P1 insuring it is above its stall condition by automatically dumping the excess flow. This guarantees that pump P1 is always operating above the stall condition. Pressure transducer 2 (PT2) can be used to monitor the pressure controlled by pressure regulator PR1. Pressure transducer PT2 can be used as part of the diagnostics for the device. Solenoid 1 (Sol1) can be used during start up to isolate the system to enable a leak checking during the startup mode. Since for normal operation it may be desirable to have solenoid Sol1 open, a normally open (NO) solenoid may be used.

If solenoid Sol1 were to fail, some portions of the leak checking feature would be lost, but the system could still safely deliver NO therapy to the patient. The check valve before the output to the cassette is included in order to insure that if the system were powered off with the cassette still inserted in the device, $NO_2$ could not backstream into the ventilator injector flow section, and possibly form nitric acid which over a long period of time could damage some of the components.

Another aspect of the design of the device is that the system can automatically detect running out of the source $N_2O_4$ with a thirty minute warning of reserve material being present. The primary warning and/or alarm that the system is about to run out of $N_2O_4$ comes from temperature control system which determines the amount of $N_2O_4$ remaining in the cassette based on the temperature, time and dump information generated during use of the device. When the liquid in the stainless steel vessel is used up, then the $N_2O_4/NO_2$ vapor remains, filling the internal volume. The vapor is under pressure because the vessel is hot. Experiments have determined that this gaseous $N_2O_4/NO_2$ vapor acts as a reservoir and still can be effectively used to deliver NO therapy to the patient, for up to 30 minutes after the liquid level has been depleted. It is like the warning on a gas gauge in a car, namely that you are about to run out of gas and that you have less than 30 minutes to get the back up unit activated.

In this condition, a feedback loop can keep increasing the vessel temperature to maintain the proper NO concentration, since there is no more reservoir of liquid remaining to replenish the material in the gas phase. As the amount of $NO_2$ within the vessel decreases, the temperature needs to increase to maintain a constant pressure of $NO_2$ and thus a constant flow of $NO_2$ through the restrictor and a resultant constant concentration of NO to the patient. A temperature control monitor can readily determine that the device is operating in this "reserve gas tank mode" from the characteristics of the continuous temperature increases that are required to maintain the NO concentration. The software controlling the device can use the temperature increase required to maintain constant NO to determine that a message should issue to indicate to the operator that the reservoir is dry and that there are less than 30 minutes of NO supply remaining in the unit. The message could request that the operator immediately activate a standby console and to immediately switch to the stand by console. The ability to predict that the supply of NO is nearly gone provides an additional safety net to the user.

In an embodiment, the integrated value of the current drawn with time to maintain NO delivery can reflect the amount of liquid $N_2O_4$ remaining in the device. Thus, monitoring the current drawn can operate as a "fuel gauge," allowing the user or device to monitor the amount of operating life remaining in the cartridge. In traditional gas systems, the regulator on a gas tank has a dial pressure gauge which is used to determine the pressure of gas remaining in the tank, and this functions as a fuel gauge. Instead of a dial gauge, some systems use electronic pressure gauges which are then used to display the amount of gas (the pressure) remaining in the tank. In the devices described herein, a "fuel" gauge for the liquid level is needed so that the operator can determine how many more hours the cassette will last at the current usage rate, before it is empty.

In one example, a measure based on time alone is inadequate because the system could be dosing at 1 ppm at 4 L/min during the weaning of a neonatal patient, or at 40 ppm when dosing an adult at 12 L/min. Actual usage of the $NO_2$ can be calculated and the output displayed as a "fuel" gauge on the front panel of the device. The hotter the liquid-containing vessel, the higher the internal pressure and the more $NO_2$ is pushed out of the vessel. The internal computer can track the temperature and the length of time that the vessel was at that temperature. Based on historical data, the internal computer can then calculate how much $NO_2$ had been removed from the vessel, provided that typical emission rates at different temperature has been determined for the restrictor length and diameter used in the device. The computer then has the necessary information to calculate the amount of $NO_2$ remaining behind in the vessel, by subtracting the amount used from the amount of liquid that was present in the liquid source (for example, glass ampoule).

Under certain circumstances, two key corrections can be made to calculations performed by the computer. The first correction can be the temperature difference (delta T) between the restrictor tubing and the liquid vessel. If the delta T is greater than a nominal 8° C. delta T, then less material will have been vaporized out of the vessel. The cartridges in the cassette can have a fixed lifetime once they have been exposed to the oxygen in the air, which slowly begins to oxidize the antioxidant. This is not an issue at 24 hours, but will be if the cassette is used after, for example, one week. Thus, the fuel gauge of the cassette will have a maximum lifespan, regardless of how much liquid $NO_2$ was remaining.

Another adjustment can arise because of flushing during cassette removal and shutdown. When the cassette is removed, the lines still have NO and air in them, primarily in the injection flow section of FIG. 1. This NO, in the presence of the oxygen in the air, will be oxidized to $NO_2$, which will form nitric acid in the presence of moisture from the air. This can lead to having nitric acid in the lines. Over short periods of time this nitric acid would not be a problem, but over the long term when the console is in storage, it could damage some of the internal components like the hot wire flow sensors. In order to eliminate the possibility of nitric acid being formed and reaching a level which could cause damage, a flushing procedure can be performed every time a cassette is removed. This can happen automatically upon removal of the cassette from the device and need not rely on activation by the user. Referring to FIG. 1, when the cassette is removed, solenoid sol6 can be initially closed, and proportional valve pv1, proportional valve pv2 and solenoid sol5 can be opened, and pump p2 can be turned on forcing pure air through the dilution line which can be exhausted through the output line where the cassette could connect to the console. This flush can be performed for about 15 seconds at which time proportional valve pv1 is closed and sol6 opened for two seconds to momentarily flush the short line between the tee fitting at sol6 and the output line. The computer can be configured with software that is setup in such a way that a controlled shutdown cannot occur unless the cassette has been removed, and a reminder message is generated if the operator tries to shut the system down without removing the cassette.

In some embodiments, it is possible to monitor voltage applied to one or more of the proportional valves to check for leaks. Based upon experimental data, the voltage required to open the proportional valves to achieve a given flow of gas through the valve at a given input pressure is reproducible and can be characterized. If the operating voltage for either of the two proportional valves, PV1 or PV2, is outside of the expected normal operating range, it can indicate that a leak had occurred during operation and subsequent to leak test on start up. Thus, if there were a leak after flow sensor FS1 the flow through flow sensor FS1 would increase and thus proportional valve PV1 or proportional valve PV2 could be commanded to close more than is expected, and thus the operating conditions of proportional valve PV1 and/or proportional valve PV2 would be outside the nominal window. If this condition were to occur, an error message is generated.

In some embodiments, it is possible to check on the calibration of flow sensor FS1 and flow sensor FS2. During the initial flush of the cassette immediately after it has been activated, 100% of the air flow goes both through flow sensor FS1 and flow sensor FS2. The readings of both of these flow sensors should be identical, within experimental error. If the two flow sensors do not give the same readings, then either one of the sensors is not working properly, or there is a leak in their flow path. This information can be used to cause an error message transmitted to the user to have the console taken out of use for service. If the problem persists, then there is a leak in the gas circuit. However, if the device is able to supply the set point NO concentration, and if the ventilator is working properly, then the device can be left on line until the current cassette has been depleted, at which time it should be swapped out and serviced.

In another aspect, the device includes two independent NO sensors. This can simplify calibration of the NO sensors, since it provides the ability to calibrate while the device is dosing the patient while still monitoring the NO output, and also provides instant feedback of NO sensor failure, if the two sensors readings do not agree within an acceptance window.

Figure 2:
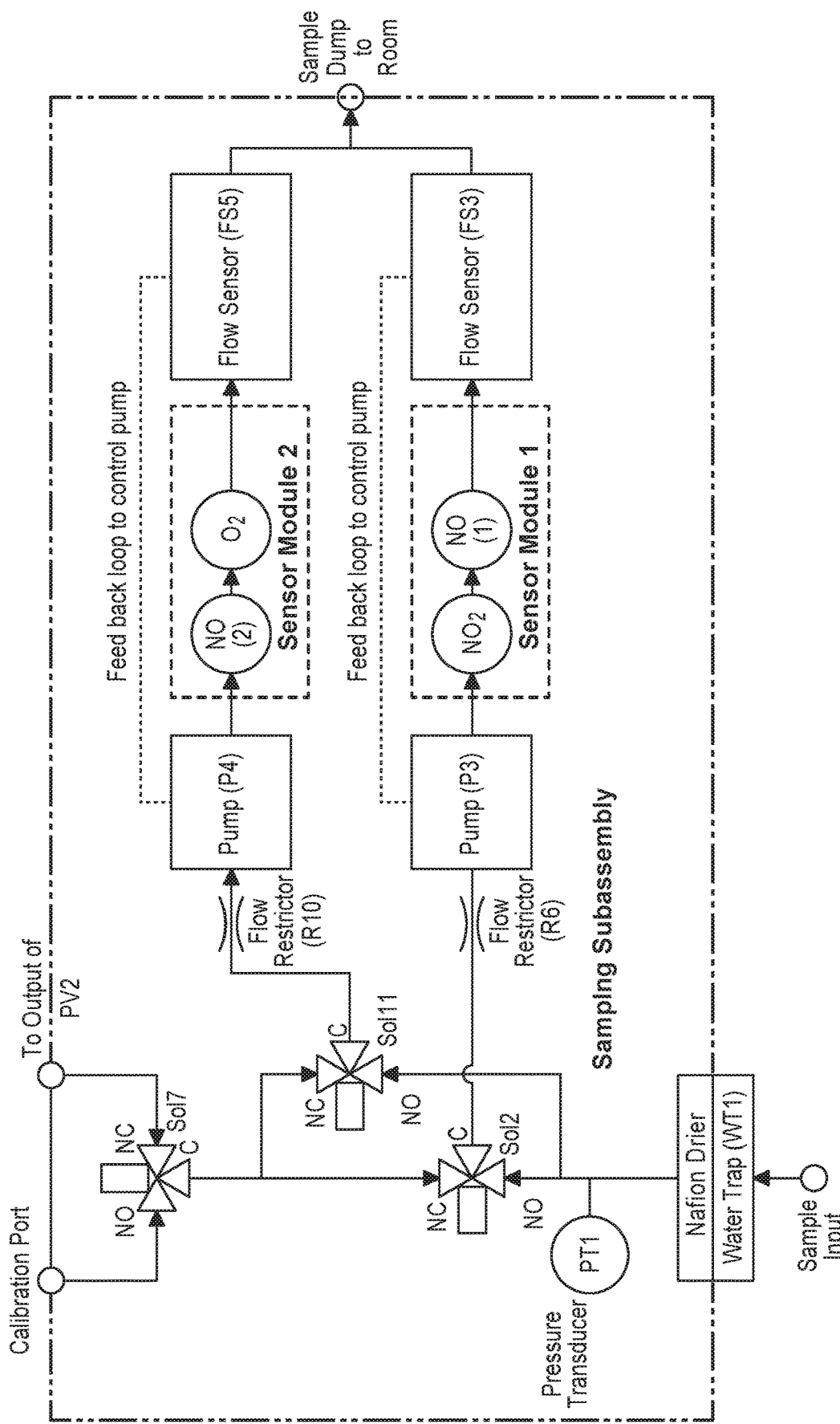
FIG. 2 is a schematic illustration of a sampling portion of an NO delivery device, according to an embodiment.

Referring to FIG. 2, the gas sample flow path has two independent sample paths. Each path includes a dedicated sample pump, flow sensors and controllers. The duplicate sample paths allows for the independent measurement of NO with two completely independent electrochemical sensors. The two NO sensors can be set up so that one does the measurement and the other is for comparison only. Since the two NO sensors are independent of each other, it is as if the system executes continuous checking of the need for calibration since if one NO sensor drifts or fails the machine will know about it quickly and can accommodate the problem. In other words, the two independent NO sensors can increase the system reliability, since if one fails the other can take over. By employing a second NO sensor, the system provides the ability to calibrate while dosing, while still monitoring the NO. The device configuration shown in FIG. 2 represents one possible flow scheme. Another device configuration could be to have two $NO_2$ sensors, or to have the $O_2$ sensor in other locations in the flow path.

The device configuration provides stability in the instance of loss of one of the NO sensors. If there is a significant difference between the measurement of the control/alarm and confirm NO sensors, an error message can be generated. If the failure is due to one of the flow paths, such as a failure of the sample flow sensor, the sample pump, the NO sensor itself or the electronics associated with the pump, flow sensor or sensor, then it may be obvious and the other NO sensor can safely take over. If the data do not clearly indicate which sensor is out of calibration, it may be possible to determine which NO sensor has failed by comparing the NO response to the unique $NO/NO_2$ data from a kinetic equation described, for example, in U.S. Provisional Patent Application No. 62/699,774 filed Jul. 18, 2018, the disclosure of which is incorporated herein by reference. If this can identify the failed sensor, then the device can continue operation until the cassette empties, at which time a new console needs to be used should be replace, or at least the sensor module should be replaced and calibrated. If this protocol does not identify an error with the NO sensor, it may be necessary to recalibrate the NO sensors.

The device configuration provides stability, with the $NO_2$ sensor serving as the fourth line of defense. In the NO delivery device, the $NO_2$ sensor is another line of defense in preventing a patient from receiving $NO_2$. There can be multiple protections in place to avoid $NO_2$ delivery to the patient. The first is the initial primary cartridge in the cassette which is sized to have considerable reserve capacity in handling the entire liquid $NO_2$ contents of the cassette. The second is the second back up cartridge in the cassette which serves as 100% back up to the primary cartridge. It also has reserve capacity and can convert the entire $N_2O_4$ contents on its own. The third is an in-line cartridge in the flow line from the ventilator to the patient. A similar, but much smaller, inline cartridge can be used for use with a nasal cannula. This in line cartridge also has the reserve capacity to convert the entire liquid contents of the cassette into NO. In some embodiments, the in line cartridge can be replaced by a mixer with no active chemistry, made from a very high surface area material like silica gel. The fresh silica gel has enough surface area to physically adsorb the "sticky" $NO_2$ that may be formed in the gas lines to the patient. The fourth, and final defense is the $NO_2$ sensor, where the sample is taken as close as possible to the patient. If this sensor detects $NO_2$, it triggers an alarm and stops the flow. For these reasons, the $NO_2$ sensor is not considered a critical component, since two or three other independently manufactured and tested chemical systems would have to fail before it became life critical. Furthermore, chemistry systems are far less likely to fail than sensitive electrochemical sensors which rely on power supplies, electronics and computer control. It is highly unlikely that all three critical components would fail at the same time.

Similar to the NO sensors, the $NO_2$ sensor could give a full scale reading or zero output indicating a complete $NO_2$ sensor failure. Since the design of the NO delivery device is such as to minimize the $NO_2$ concentration in a ventilator line, a failure of the $NO_2$ sensor can cause an alarm and while the operator will be notified to replace the failed console, and eventually the sensor module in the console, dosing will continue, and the operator can perform a standard transition with a standby or backup unit rather than go into an emergency backup mode. For the $NO_2$ sensor there need not be a second sensor, and while the system can be designed to minimize the amount of $NO_2$ by the use of not one but three $NO_2$ to NO converting cartridges, there need not be a secondary confirmation that they are operating properly, thus the recommendation to replace the faulty console. However, the console could be replaced using the normal transition from one console to another and not the fast backup transition.

During long periods of continuous use, drift in the output current of the electrochemical NO sensors can occur, due to saturation and other factors, causing errors in the ability of the sensor to accurately measure the NO concentration. To correct for this drift, it may be desirable that the sensor be exposed for an extended period of time (hours) to ambient air and/or a source containing zero concentration, allowing the sensor to de-saturate (see, for example, U.S. Pat. No. 9,279,794, entitled "Systems and Methods for Compensating Long Term Sensitivity Drift of Electrochemical Gas Sensors Exposed to Nitric Oxide," the disclosure of which is incorporated herein by reference). One way to resolve this difficulty is to use two identical delivery consoles, one for delivery and one for standby-backup. When the cassette is exhausted the system can switched to the standby-back up console which then becomes the primary console and the former primary console becomes the standby-back up console. While the use of the two console provides 100% backup in the case of failure, it also overcomes the overuse and desaturation of the sensor issue, since when in standby-backup, the sensors in that console can desaturate and "rest." This is a significant reason for having 100% redundancy of the sampling sensors, their pumps and flow sensors, all 100% independent of the other set of sensors.

When the NO delivery device is used to introduce NO into a ventilator line, the device can use air as a make-up gas so that the device gas injection does not significantly alter the total gas flow to the patient. In order to insure that the NO injection does not perturb the ventilator settings to the extent that it may disturb the ventilator, the injection flow from the device is typically maintained to be less than 10% of the total flow to the patient. The ventilator typically is flowing gas to the patient with enhanced oxygen content. The NO delivery device injects the NO in air at nominally 21% oxygen. Thus, except for the case where the ventilator is supplying gas to the patient at 21% oxygen, there is some dilution of the oxygen content of the ventilator gas being supplied to the patient. This dilution is given by the following equation:

$$\text{Percent } O_2 \text{ to Patient} = [\{\% O2/100 + (Flowinj/Flowvent) \times 0.21\}/\{1 + Flowinj/Flowvent)\}] \times 100$$

Where:
Flowinj=Injection flow in same units as ventilator flow
Flowvent=Ventilator flow in same units as injection flow
% $O_2$=Percent oxygen out of ventilator
0.21=Fraction of oxygen in injection flow (21%)

Under typical conditions of the ventilator being set to deliver 60% $O_2$, the $O_2$ concentration at the patient can be reduced to 58.1% with the NO delivery device providing 5% of the total flow. With the NO delivery device proving 10% of the total flow at 60% $O_2$, the $O_2$ concentration would be reduced to 56.5%. Under the worst case condition of the ventilator delivering 100% $O_2$ to the patient and the NO delivery device providing 10% of the flow to the patient, the concentration of $O_2$ going to the patient would be 92.8% instead of 100%.

A significant reason for having an $O_2$ sensor in the NO delivery device is because for systems based on compressed gasses of NO in nitrogen, there is a possibility that in the event of a malfunction the patient could be asphyxiated with nitrogen and zero oxygen. In the case of delivering NO based on liquid $N_2O_4$, the NO is delivered in air, so it is not possible to have the patient receive gas that is ever less than 21% $O_2$, which provides a level of patient safety that cannot be achieved in $NO/N_2$ sourced systems. Furthermore, the oxygen sensor is not critical for the operation of the NO delivery device. Based upon the known ventilator and injection flow, and the oxygen sensor embedded in the ventilator, the health care provider can compute the small decrease in oxygen percent due to the injection of gas with only 21% oxygen into the ventilator line. Thus, if the oxygen sensor were to fail, the NO delivery device would continue operating and supplying NO therapy without interruption to the patient, while still issuing a warning message notifying the operator that the oxygen sensor was not operating properly.

The detection of a failure of the $O_2$ sensor could be based upon a span check or calibration failure, or based upon the output of the oxygen sensor being outside of its expected range. The faulty console or possibly just the failed sensor module could then be replaced at a convenient time, after the cassette is depleted.

The NO delivery device can operate in ppm delivery mode or microgram deliver mode. During normal mode operation, if the cassette is operating under constant conditions, the number of molecules being generated per unit time is constant. If the patient's breathing rate is constant and not varying, the number of micrograms being presented to the patient is constant and the number of micrograms inhaled by the patient is constant, being some fixed portion of what is being delivered. If the flow from the ventilator were to change, the number of molecules and thus the number of micrograms being presented to the patient per unit time remains constant. However, changing the flow rate of the ventilator would cause the dilution (lower ppm) or concentration (higher ppm). The normal operation of the NO delivery device can be to use a feedback loop driven by the output of the NO sensor, which is in ppm. The loop can maintains the ppm constant by triggering a correction to either or both the vessel temperature and the scrubbed bypass portion of the device. Keeping a constant ppm may or may not be what the health care provider wants. With other drugs the health care provider controls the dose in terms of micrograms actually inhaled by the patient. If the dosage is micrograms per unit time that is desired to be held constant, the algorithm logic can do this automatically, but the device needs to be provided the ventilator flow rate. In order to do this, the flow rate from the ventilator needs to be measured and sent to the NO delivery device computer. This signal can come from the ventilator itself, or from a special flow sensor in the ventilator line to the patient.

The NO delivery device can include a protocol for automated detection of occlusion of a sampling line. See, for example, FIG. 2. The sample line from near to the patient to the NO delivery device should never be occluded so as to prevent or even partially block the flow from the patient sampling point to the analytical module in the NO delivery device. Similarly, it is of critical importance that the sampling line never be disconnected to develop a significant leak. Without a correct NO reading from the patient, the feedback loop on which control is based would lack vital information and not be aware that there had been a failure.

From information from the differential pressure transducer PT1, as well as pump P3 and/or pump P4 operating conditions and the flow measured by flow sensor FS3 and or flow sensor FS5, an occlusion of the sample line can be determined and an alarm issued. A blockage or partial blockage would present itself as one or more of the following: a slower flow rate, more power for the pump to draw at the same flow rate, a change in the pulsing peaks and valleys on the pressure transducer. Information from the differential pressure transducer can also help determine if the sample line is not connected, since for the ventilator application, the pulses will not be present. It is also possible to detect a leak in the sample line as a higher flow for the same power to the pump, or decreased. For the ventilator application, the baseline pressure measured with a sample line and without would be different.

In certain circumstances, the ratio of $O_2$ to air can be used to measure $NO_2$ formation in gas lines. The rate equation for the formation of $NO_2$ from the oxidation of NO with oxygen shows that the rate of formation of $NO_2$ is proportional to the oxygen concentration, the square power of the NO concentration and time. This is a well-known fact for over 100 years. The linear proportionality of the formation rate of $NO_2$ to the $O_2$ concentration can be used to advantage to answer critical questions, such as to determine where in the process the $NO_2$ came from.

$NO_2$ can come from multiple sources. If the source of the NO is a gas cylinder, then there may be an impurity of $NO_2$ in the NO itself, including from $NO_2$ temporarily adsorbed on the walls of the container and then being released. If the source of NO is $N_2O_4$, then it may come from breakthrough of the $NO_2$ in the cartridge, where unreacted $NO_2$ passes through the cartridge. Similarly, for other sources of NO, there may be an impurity in the source itself. If the source of NO is an electric arc of some type, then the source could come from the arc itself. If the source of the NO is a chemical reaction such as the reaction of nitrite with an acid, then the $NO_2$ could be formed as a byproduct of the reaction. Other sources of $NO_2$ can include $NO_2$ that was temporarily adsorbed on the walls of the tubing, and was released due to temperature differences, gas turbulence at the wall, or for any chemical/mechanical reason. This could happen in the connecting tubing, in the sample lines to the analysis module, or inside the chemical analysis equipment itself. The latter possibility has been shown to occur inside a chemiluminescent analyzer and inside a CAPS instrument. Moisture can act as a trap for the $NO_2$, forming nitric and nitrous acids. $NO_2$ could be lost by the reaction of NO with $NO_2$ to form $N_2O_3$. The reverse reaction is also possible in some circumstances where $N_2O_3$ can decompose to form NO and $NO_2$. The $NO_2$ could be formed by the reaction of NO with oxygen gas inside the gas plumbing.

The method may involve measuring the $NO_2$ level using at least two different $O_2$ concentrations. Most often air (21%

$O_2$), nitrogen (0% $O_2$) and pure $O_2$ (100%) can be used. By varying the fraction of $O_2$ in the gas lines, or adding additional $O_2$ at different parts of the process, it can be possible to determine how much of the $NO_2$ was formed in the gas lines. The effect is similar to the observer effect in physics which notes that measurements of certain systems cannot be made without affecting the systems, that is, without changing something in a system. In this case, when a sample is removed and sent to a detector, the NO and $O_2$ continue to react to form $NO_2$. The NO and $NO_2$ reported by the detector do not reflect the values at the sampling site unless the data has been corrected to account for the amount of NO lost during the process to $NO_2$. Depending upon the levels and the situation, the effect can be dominant.

By measuring the difference in the $NO_2$ levels with at least two different $O_2$ levels it is possible to back calculate how much of the $NO_2$ was formed in the gas lines. If the gas was then inhaled by the patient, there is little that can be done to correct the situation, apart from using an antioxidant cartridge to eliminate the $NO_2$. If the formation occurred in the gas sampling lines to an instrument, then the method described here can be used to correct the data so as to give the true reading at the sample point, and take out the formation that occurred due to the very act of removing the sample.

For example, when monitoring the $NO_2$ level after the in-line cartridge and just before the patient with the ultra-sensitive CAPS spectrometer, it was shown that almost all of the $NO_2$ that was being reported was being formed in the sample lines to the detector, and that there was essentially less than 0.008 ppm (8 ppb) present at the patient. In another example it was found that various "dead" zones in the sampling line were causing the $NO_2$ levels to be artificially high. The zones were due to a T branch where sample was trapped and then released.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed:

1. A method, comprising:
coupling a cassette configured to provide NO gas to a console containing a pump and a first flow sensor, the cassette coupled to the console such that the first flow sensor is disposed between the cassette and the pump;
closing an output solenoid that is disposed after the cassette, the output solenoid, when open, configured to allow gas, including NO gas, to be conveyed to a patient, closing the output solenoid configured to place the cassette in fluid communication with a second flow sensor disposed between the cassette and an exhaust port;
activating the pump; and
leak testing the cassette by comparing a flow rate measured by the first flow sensor to a flow rate measured by a second flow sensor.

2. The method of claim 1, further comprising:
removing the cassette; and
operating the pump after removing the cassette to flush the first flow sensor and the second flow sensor.

3. The method of claim 1, further comprising:
opening the outlet solenoid;
operating the pump to produce a flow of gas that passes through a gas accumulator and a restrictor to abate pressure pulses; and
delivering the gas, including NO gas, to the patient after opening the outlet solenoid.

4. The method of claim 1, further comprising:
closing a proportional valve disposed between the cassette and the second flow sensor;
operating the pump to increase a pressure in the cassette;
once the pressure in the cassette reaches a threshold, turning off the pump; and
pressure testing a seal between the cassette and the console by measuring a rate at which the pressure in the cassette decreases after turning off the pump.

5. A device, comprising:
a vessel containing liquid $N_2O_4$;
a heater configured to heat the vessel and the liquid $N_2O_4$ contained therein to produce $NO_2$ gas;
a liquid $N_2O_4$ monitor operatively coupled to the heater and configured to monitor at least one of the current or the voltage applied to the heater, the liquid $N_2O_4$ monitor configured to determine when the liquid $N_2O_4$ in the vessel has been depleted and only $NO_2$ gas remains based on at least one of a current or a voltage drawn by the heater; and
a leak detector configured to identify a leak based on voltage drawn by a valve in the device.

6. The device of claim 5, wherein the liquid $N_2O_4$ monitor is configured to monitor a temperature of the vessel containing liquid $N_2O_4$.

7. The device of claim 5, further comprising a NO availability gauge that displays output from the liquid $N_2O_4$ monitor.

8. The device of claim 7, wherein the NO availability gauge is configured to alert a user to replace a cassette that includes the vessel based on a time and temperature history of the vessel.

9. The device of claim 5, further comprising an NO dosing display in micrograms per minute or parts per million.

10. The device of claim 9, wherein the NO dosing display is corrected for formation of $NO_2$.

11. The device of claim 10, wherein the NO dosing display is corrected by varying one or more of an amount of $O_2$ in a sample, a length of the sampling lines, or a volumetric flow rate in the sampling lines.

12. The device of claim 5, further comprising:
at least one of a leak or blockage detector, the at least one of the leak or blockage detector configured to monitor one or more of a change in the size and frequency of pressure pulses in an output line.

13. A method, comprising
coupling a NO source cassette that includes (i) liquid $N_2O_4$ and is configured to produce $NO_2$ gas and (ii) a conversion cartridge configured to convert the $NO_2$ gas to provide NO gas to a console such that the NO source cassette is configured to receive air from a pump via an input and provide NO gas via an output;
closing a solenoid between the output of the NO source cassette and a patient interface to isolate the NO source cassette from an exterior of the console;
operating a pump to increase a pressure in the NO source cassette;
once the pressure in the NO source cassette reaches a threshold, turning off the pump; and pressure testing a seal between the NO source cassette and the console by measuring a rate at which the pressure in the NO source cassette decreases after turning off the pump.

* * * * *